United States Patent [19]

Seiler et al.

[11] Patent Number: 4,595,697
[45] Date of Patent: Jun. 17, 1986

[54] TREATMENT OF SEIZURE DISORDERS AND PHARMACEUTICAL COMPOSITIONS USEFUL THEREIN

[75] Inventors: Nikolaus Seiler; Shakir Sarhan, both of Strasbourg, France

[73] Assignee: Merrell Dow Pharmaceuticals Inc., Cincinnati, Ohio

[21] Appl. No.: 705,955

[22] Filed: Feb. 27, 1985

Related U.S. Application Data

[62] Division of Ser. No. 594,079, Mar. 28, 1984, Pat. No. 4,540,582.

[51] Int. Cl.[4] ............................................. A61K 31/24
[52] U.S. Cl. .................................................... 514/534
[58] Field of Search ....................................... 514/534

*Primary Examiner*—Stanley J. Friedman
*Attorney, Agent, or Firm*—William J. Stein

[57] ABSTRACT

Glycine, sarcosine, or N,N-dimethylglycine exerts a synergistic effect upon gamma-vinyl GABA for the treatment of seizure disorders, in particular epilepsy.

10 Claims, No Drawings

TREATMENT OF SEIZURE DISORDERS AND PHARMACEUTICAL COMPOSITIONS USEFUL THEREIN

CROSS-REFERENCE TO RELATED APPLICATION

This is a divisional of application Ser. No. 594,079, filed Mar. 28, 1984, now U.S. Pat. No. 4,540,582.

Gamma-aminobutyric acid (GABA) is a major inhibitory neurotransmitter of the CNS. Various theories have been advanced to implicate deficiencies in GABA-mediated neuronal inhibition as a contributing factor in the pathogenesis of seizure disorders, such as epilepsy. In laboratory animals, a decrease in CNS GABAergic activity leads to convulsions while an increase in CNS GABA concentrations protects against seizures (B. Meldrum, *Lancet* 1978:II: 304–306 and L. Spero, *Lancet*:1982: 1319–1322). The mechanism of action of many anti-seizure agents can be explained by the causation of effects which ultimately result in augmented GABAergic function [L. Spero, supra; P. Schechter et al. in *Enzyme-activated Irreversible Inhibitors*, N. Seiler, M. Jung, and J. Koch-Weser, Eds., Elsevier/North-Holland Biomedical Press, Amsterdam, N.Y. Oxford 1978, pp. 148–162; S. Sarhan et al., *J. Neurosci. Res.*, 4, 399–421 (1979); K. Gale et al., *Science*, 208, 288–291 (1980); and N. Seiler et al., in *Neurochemistry and Clinical Neurology*, L. Battistin, G. Hashim, and A. Lajtha, Eds., Alan R. Liss, New York, 1980, pp. 425–439].

GABA and its precursors do not readily cross the blood-brain barrier. However, one approach to increasing GABA concentrations in the CNS is by blocking its catabolism. It is known that gamma-vinyl GABA (4-amino-hex-5-enoic acid), hereinafter referred to as GVG, is a selective enzyme-activated irreversible inhibitor of GABA-transaminase (GABA-T) [B. Metcalf, *Biochem. Pharmacol.*, 28, 1705–1712 (1979) and B. Lippert et al., *Eur. J. Biochem.*, 74, 441 (1977)], the enzyme responsible for GABA catabolism. Administration of GVG to laboratory animals produces dose-related increases of GABA concentrations in the brain [M. Jung et al., i J. Neurochem., 29, 797–802 (1977); P. Schechter et al., *Europ. J. Pharmacol.*, 45, 319–328 (1977); and M. Jung, in *Enzyme-activated Irreversible Inhibitors*, N. Seiler, M. Jung, and J. Koch-Weser, Eds., Elsevier/North-Holland Biomedical Press, Amsterdam, N.Y. Oxford, 1978, pp. 135–148] and in cisternal cerebrospinal fluid (CSF) [P. Böhlen et al., *Brain Res.*, 167, 297–305 (1979)]. In man, treatment with oral GVG produces increases in the GABA concentrations of CSF obtained via lumbar puncture [J. Grove et al., *Life Sci.*, 28, 2431–2439 (1981)]. Further, GVG displays anticonvulsant activity in a variety of anti-seizure models in animals [P. Schechter et al., in *GABA-Biochemistry and CNS Functions*, P. Mandel and F. DeFeudis, Eds., Plenum, New York, 1979, pp. 43–57; M. Palfreyman et al., *Biochem. Pharmacol.*, 8, 817–824 (1981); P. Schechter et al., in *Enzyme-activated Irreversible Inhibitors*, N. Seiler, M. Jung, and J. Koch-Weser, Eds., Elsevier/North-Holland Biomedical Press, Amsterdam, N.Y. Oxford, 1978, pp. 148–162; and B. Meldrum, *Clin. Neuropharmacol.*, 5, 293–316 (1982)]. Moreover, clinical studies in man have demonstrated that daily doses of 1 to 4 g of GVG in divided doses (usually twice daily) administered to epileptic patients refractory to conventional anti-seizure medicaments produced a decrease in the frequency and severity of seizures.

The present invention provides an improved method and pharmaceutical compositions for treating seizures, such as those associated with epilepsy.

In its method of treatment aspect, the invention comprehends a method for controlling seizures in a patient in need thereof which comprises administering to said patient in combination:

(a) an effective amount of gamma-vinyl GABA, or a pharmaceutically acceptable salt thereof, and (b) an effective amount of glycine, sarcosine (N-methylglycine), or N,N-dimethyl-glycine, or a $C_1$–$C_8$ alkyl ester thereof, or a pharmaceutically acceptable salt thereof.

As used herein, the term "seizures" includes both convulsive and non-convulsive seizures associated with, for example, epilepsy, trauma, drug withdrawal (e.g. alcohol withdrawal, barbiturate withdrawal, and benzodiazepine withdrawal), tetanus, metabolic disease, elevated body temperature, drug induction (e.g. theophylline), and porphyria. The treatment of seizures associated with epilepsy is a preferred embodiment of this invention. The term "controlling" means decreasing the severity and/or the frequency of the seizures.

The term "$C_1$–$C_8$ alkyl" means a straight or branched alkyl moiety having from one to eight carbon atoms, for example, methyl, ethyl, propyl, isopropyl, butyl, isobutyl, pentyl, hexyl, or octyl. Preferred alkyl groups are those having from one to four carbon atoms, especially methyl or ethyl. The $C_1$–$C_8$ alkyl esters of glycine, sarcosine or N,N-dimethylglycine are either known compounds or can be made by conventional means.

Illustrative examples of pharmaceutically acceptable salts of the compounds employed in this invention include:

(a) non-toxic acid addition salts formed with inorganic acids, such as hydrochloric, hydrobromic, sulfuric, and phosphoric acid; or with organic acids, such as organic carboxylic acids, for example, salicylic, maleic, malonic, tartaric, citric, and ascorbic acids, and organic sulfonic acids, for example, methane sulfonic acid; and (b) non-toxic salts formed with inorganic or organic bases, such as hydroxides of alkali metals, for example, sodium, potassium, and lithium, alkaline earth metals, for example, calcium and magnesium, light metals of Group III A, for example, aluminium, organic amines, such as primary, secondary, or tertiary amines, for example, cyclohexylamine, ethylamine, methylamino-ethanolamine and piperidine.

The salts are prepared by conventional means.

As employed herein and in the claims, "gamma-vinyl GABA" (GVG) refers to S-gamma-vinyl GABA (S-GVG) or to mixtures of S-gamma-vinyl GABA with R-gamma-vinyl GABA, such as the racemate, (R,S)-gamma-vinyl GABA (R,S-GVG). R-GVG does not irreversibly inhibit GABA-T. Thus, R-GVG in a form free from S-GVG is not useful for the purposes herein-described. Unless otherwise indicated, the dosages expressly set forth at various places herein are applicable to R,S-GVG. As will be obvious to those skilled in the art, the dosages applicable to S-GVG will be about one-half of the dosages applicable to R,S-GVG.

The effect of the administration of GVG in combination with glycine, sarcosine, or N,N-dimethylglycine, or an alkyl ester or salt thereof, in controlling seizures is synergistic in that administration of the combination gives greater control of seizures than is possible with administration of the individual compounds. The synergistic effect of glycine, sarcosine, or N,N-dimethylglycine, or a ester or salt thereof, upon GVG in the treatment of seizures permits GVG to be administered in general at dosage levels significantly lower than those required with GVG alone. Moreover, the administration of glycine, sarcosine, or N,N-dimethylglycine, or an ester or salt thereof, in combination with GVG gives a greater incidence of control of seizures than is attainable with GVG alone at the same dosage level.

Suitable dosages of GVG, glycine, sarcosine, or N,N-dimethylglycine, or an ester or salt thereof, will be any amount that is effective for decreasing the severity and/or the frequency of seizures in the afflicted patient. The effective dosage will vary according to the general condition of the patient and the specific nature, severity, and/or the frequency of the seizure.

In general, when combination therapy is used for the control of seizures, the effective dosage of GVG can be decreased by a factor of from 2 to 5. Thus, the effective dose of GVG, such as in the treatment of epileptic seizures, will be in the range of about 0.2 to 2 grams per day, preferably given in divided doses, orally.

In general, the effective dosage of glycine, sarcosine, or N,N-dimethylglycine, or an ester or salt thereof, will be in the range of about 2 to 12 grams per day, preferably in divided doses, orally. A preferred dosage range is 3 to 4 grams per day. Since glycine is non-toxic, there is no upper limit to the daily effective dose other than the limit of practical considerations.

It will be understood that glycine, sarcosine, or N,N-dimethylglycine, or an ester or salt thereof, can be administered in combination with GVG in several ways. Preferably, glycine, sarcosine, or N,N-dimethylglycine, or an ester or salt thereof, can be administered simultaneously with GVG. However, glycine, sarcosine, or N,N-dimethylglycine, or an ester or salt thereof, can be also administered prior to the time of administration of GVG or in between the times of administration of GVG.

For the treatment of epileptic seizures, GVG is given preferably in divided doses twice daily. However, GVG may also be given once daily, or even once every other day, depending upon the particular patient.

It will also be understood that the method of this invention can be employed with patients who are receiving other anti-seizure medications, when the seizures are not fully controlled by the such medication, provided, of course, that there are no adverse drug interactions.

The active compounds, as described herein for the combination therapy of seizures, can be administered in various manners to achieve the desired effect. The active compounds can be administered separately or in mixtures with each other. Preferably, the active compounds are administered with pharmaceutically acceptable carriers or diluents, the proportion and nature of which are determined by the solubility and chemical properties of the compounds, the chosen route of administration, and standard pharmaceutical practice. The active compounds, either separately or in mixtures, may be administered orally in solid dosage forms, e.g. capsules, tablets, powders, or in liquid forms, e.g. solutions or suspensions. The active compounds may also be injected parenterally in the form of sterile solutions or suspensions. Solid oral forms may contain conventional excipients, for instance: lactose, sucrose, magnesium stearate, resins, and like materials. Liquid oral forms may contain various flavoring, coloring, preserving, stabilizing, solubilizing, or suspending agents. Parenteral preparations are sterile aqueous solutions or suspensions which may contain various preserving, stabilizing, buffering, solubilizing, or suspending agents. If desired, additives, such as saline or glucose may be added to make the solutions isotonic. Sustained-release dosage forms may also be employed.

The term "unit dosage form" is used herein to mean a single or multiple dosage form containing a quantity of the active ingredient in admixture with or otherwise in association with the diluent or carrier, said quantity being such that one or more predetermined units are normally required for a single therapeutic administration. In the case of multiple dose forms, such as liquids or scored tablets, said predetermined unit will be one fraction such as 5 ml (teaspoon) quantity of a liquid or a half or quarter of a scored tablet, of the multiple dose form.

In the first composition aspect of the invention, there are provided pharmaceutical formulations for use in the method herein-before described, in which form the active compounds will preferably be utilized. Such formulations are prepared in a manner well known per se in the pharmaceutical art and will comprise: (a) an effective amount of GVG or a pharmaceutically acceptable salt thereof, and (b) an effective amount of glycine, sarcosine, or N,N-dimethylglycine, or a $C_1$–$C_8$ alkyl ester thereof, or a pharmaceutically acceptable salt thereof, either alone or in admixture or otherwise in association with a pharmaceutically acceptable carrier or diluent therefor. A carrier or diluent may be solid, semi-solid, or liquid material which serves as a vehicle, excipient, or medium for the active ingredient. Suitable diluents or carriers are well known per se. The pharmaceutical formulations may be adapted for oral or parenteral use and may be administered to the patient in the form of tablets, capsules, suppositories, solutions, suspensions, or the like. Sustained release forms of glycine, sarcosine, or N,N-dimethylglycine, or a salt or ester thereof, can also be employed.

The ratio of GVG to glycine, sarcosine, or N,N-dimethylglycine or an ester or salt thereof is in the range of from 1:1 to 1:60. Preferably, the range is from 1:3 to 1:10.

The amount of active compound present in the pharmaceutical compositions will vary and can be any effective amount. Unit doses of these compounds can contain, for example, from about 50 mg to 100 mg of GVG and from about 250 mg to 500 mg of glycine, sarcosine, or N,N-dimethylglycine, or an ester or salt thereof, and may be administered, for example, one or more times daily, as needed.

In its second composition aspect, the invention contemplates a pack comprising a quantity of pharmaceutically acceptable oral dosage forms of GVG, or a pharmaceutically acceptable salt thereof, and, separately therefrom, a quantity of pharmaceutically acceptable oral dosage forms of glycine, sarcosine, or N,N-dimethylglycine, or a $C_1$–$C_8$ alkyl ester thereof, or a pharmaceutically acceptable salt thereof. The dosage forms may be a tablet, capsule, powder, or liquid suitable for oral administration. Use of the aforesaid pack facilitate the administration of separate dosages of GVG and glycine, sarcosine, or N,N-dimethylglycine. Although the medicaments are given to the patient separately, it will be understood that glycine, sarcosine, or N,N- dimethylglycine can be administered either before the time of administration of GVG or at the same time as the administration of GVG. Glycine, sarcosine, or N,N-dimethylglycine can also be administered between the times when GVG is given. Simultaneous administration of the medicaments is preferred.

The synergistic anti-seizure effects of GVG combined with glycine, sarcosine, N,N-dimethylglycine, or an alkyl ester thereof, can be demonstrated in mice having seizures induced by the administration of 3-mercaptopropionic acid (MPA). MPA is a competitive inhibitor of glutamate decarboxylase, and its seizure effects are believed to be evoked by its specific impairment of the GABA-system [B. Meldrum, *Int. Rev. Neurobiol.*, 17, 1-36 (1975)]. The procedure employed and the results obtained in the testing of GVG combined with glycine, glycine ethyl ester, N,N-dimethylglycine, and sarcosine against MPA-induced seizures in mice are described in Example 1 to 3, Tables 1, 1a, 2, 3, and 3a, hereinafter set forth.

The anti-seizure effects of GVG and glycine were also studied in other mice seizure models, specifically (+)-bicuculline-induced seizures, metrazol-induced seizures, picrotoxinine-induced seizures, and strychnine-induced seizures. The procedures employed and the results obtained in these further tests are shown in Example 4 (bicuculline seizures), Example 5 (metrazol seizures), Example 6 (picrotoxinine seizures), and Example 7 (strychnine seizures).

The significance of the animal model seizure experiments described in Examples 1 to 7 are discussed below:

(a) Mercaptopropionic acid seizures (Tables 1, 1a, 2, 3, and 3a): From the data shown in Table 1, it can be seen that a dose of 200 mg/kg (i.p.) of GVG protects 60% of the animals against seizures induced by 40 mg/kg (i.p.) of MPA, i.e. the $ED_{50}$ of GVG is between 150 and 200 mg/kg. However, even at this dose tonic hind limb extensions were observed in 1 out of 10 animals. GVG (300 mg/kg, i.p.) protected 90% of the animals against MPA-induced seizures. Higher doses do not enhance anti-seizure effects further. On the contrary, if GVG doses were elevated above 750 mg/kg, the protection against MPA-induced seizures was clearly diminished [N. Seiler et al., in *Neurochemistry and Clinical Neurology*, L. Battistin, G. Hashim, and A. Lajtha, Eds., Alan Lin, N.Y. (1980), pp. 425-439]. As seen in Table 1, a subcutaneous (s.c.) dose of glycine, as high as 2.2 g/kg protects only 40% of the animals and 750 mg/kg (s.c.) dose of glycine protects only 20% of the animals. However, when 1.5 g (s.c.) of glycine was administered four hours after 50 mg/kg of GVG (an *ineffective* dose of GVG), complete protection against MPA-induced seizures could be achieved.

The anti-convulsive effect of glycine is short lasting. Maximal protection was obtained, approximately one hour after its administration. Two hours after glycine administration no significant anti-seizure effect could be seen, as is shown in Table 1a. The data in Table 1a were obtained after administration of glycine by gavage. The comparison of the data shown in Table 1 with those shown in Table 1a demonstrates that the mode of glycine administration has little effect on its anti-convulsive activity.

The data in Tables 2, 3, and 3a demonstrate that glycine ethyl ester, N,N-dimethylglycine, and sarcosine have a potentiating effect on GVG similar to glycine, but glycine ethyl ester and sarcosine are longer acting than glycine at an equivalent dose.

(b) Bicuculline seizures (Table 4): In previous work, GVG injected i.p. proved ineffective against seizures induced by 3 mg/kg of bicuculline (s.c.) (P. Schechter et al., In: *Enzyme-activated Irreversible Inhibitors*, N. Seiler, M. Jung, and J. Koch-Weser, Eds., Elsevier/North Holland Biomedical Press, Amsterdam, New York, Oxford, 1978, pp. 148-162). Seizures induced by intravenous administration (i.v.) of 0.55 mg/kg of bicuculline, could be antagonized by GVG [W. Buckett, *J. Pharmacol. Meth.*, 5, 35, 41 (1981)], the $ED_{50}$: 54 mg/kg. Later unpublished work indicates that the $ED_{50}$ is about 220 mg/kg.

The experiments shown in Table 4 used injections of 1.8 mg/kg of bicuculline. Table 4 shows that, with 200 mg/kg of GVG alone, a significant protective effect could be achieved, and this could be further improved by administration of glycine. However, the bicuculline test seems, on the whole, not sufficiently well reproducible probably due to a very steep dose-response curve.

(c) Metrazol seizures (Table 5): According to unpublished data, i.v. doses of 30 and 40 mg/kg of metrazol can be antagonized by GVG ($ED_{50}$ 40 and 52 mg/kg, respectively), but GVG was ineffective against 60 mg/kg of the convulsant.

In the experiment represented by Table 5, seizures were induced by i.p. injection of 75 mg/kg of metrazol. Under these conditions, all animals showed generalized clonic convulsions. The time between metrazol administration and onset of seizures was around 70 sec. An i.p. dose of 750 mg/kg of GVG, 5 h before metrazol administration did not provide protection against metrazol-induced seizures, and glycine alone was also ineffective, as was demonstrated previously. If, however, glycine was administered after GVG, the number of convulsing animals decreased with increasing doses of glycine, and the time of seizure onset was prolonged.

(d) Picrotoxinine seizures (Table 6): Picrotoxinine-induced seizures could not be influenced significantly by pretreatment with GVG or glycine or a combination of the two compounds.

(e) Strychnine seizures (Table 7): GVG at a dose of 750 mg/kg did not prevent strychnine-induced seizures, nor, was the time elapsing between the administration of the convulsant, and the onset of tonic hind limb extension significantly prolonged. A large dose of glycine (2.2 g/kg) however, prolonged the time between convulsant administration and the first seizure episode, and this time was further increased by treatment with GVG and glycine.

It will be understood that glycine, sarcosine, or N,N-dimethylglycine, or a $C_1$-$C_8$ alkyl ester or a pharmaceutically acceptable salt thereof, will produce a synergistic effect upon GABA-T inhibitors other than GVG for the control of seizures. Thus, in general, any GABA-T inhibitor can be combined with glycine, sarcosine, or N,N-dimethylglycine, or an ester or salt thereof, for the effective control of seizure disorders. In particular, the following GABA-T inhibitors, other than GVG, can be employed: (S)- or (R,S)-4-amino-hepta-5,6-dienoic acid, gamma-acetylenic GABA, aminooxyacetic acid, ethanolamine O-sulfate, gabaculine, and isogabaculine. (S)- or (R,S)-4-Amino-hepta-5,6-dienoic acid is described in UK Patent Application No. 8214290. Gamma-acetylenic GABA, aminooxyacetic acid, ethanol-amine-O-sulfate, gabaculine, and isogabacline are known compounds [See, for example, M. Palfreyman et al., *Biochem. Pharmacol.*, 30, 817 (1981)].

Inasmuch as GABA-T inhibitors are indirect GABA agonists, it is evident that direct acting GABA agonists, i.e. compounds which activate GABA receptors directly to elicit their anticonvulsant effects, may also have their anticonvulsant effects enhanced by the administration in combination with glycine, sarcosine, or N,N-dimethylglycine, or an ester or salt thereof.

The synergistic effect of glycine, sarcosine, or N,N-dimethylglycine, or an ester or salt thereof, upon a GABA-T inhibitor or a direct acting GABA agonist in the treatment of seizures, permits the GABA-T inhibitors or direct acting GABA agonist to be generally administered at dosage levels significantly lower than those required with the GABA-T inhibitor or the direct acting GABA agonist dose. Moreover, the administration of glycine, sarcosine or N,N-dimethylglycine, or an ester or salt thereof, in combination with a GABA-T inhibitor or direct acting GABA agonist provides a greater incidence of control of seizures than is obtainable using either a GABA-T inhibitor or direct acting agonist alone at the same dosage level. Suitable dosages of the GABA-T inhibitor or the direct acting GABA agonist and glycine, sarcosine or N,N-dimethylglycine, or an ester or salt thereof, will be any amount that is effective for decreasing the severity and/or frequency of seizures in the afflicted patient.

The following Examples describe the testing of GVG combined with glycine, glycine ethyl ester, N,N-dimethyl glycine, or sarcosine for the ability of the compounds to antagonize or inhibit seizures induced by MPA (Example 1, 2, 3 and 3a), (+)-bicuculline (Example 4), metrazol (Example 5), picrotoxinine (Example 6), and strychnine (Example 7).

Following interperitoneal (i.p.) doses of GVG between 100 mg/kg and 1500 mg/kg, GABA in mouse brain reaches dose-dependent levels within 5 hours which are maintained for at least the following 19 hours. Protection with GVG against chemically induced seizures was therefore always tested 5 hours after its administration.

In all the experiments, male CD1 mice (Charles River, Saint-Aubin-les-Elbeuf, France) weighing 40±4 g were used. They were kept in groups of 10 in standard plastic cages at 22° C. and 60–65% relative humidity, at a 12 h light, 12 h dark period, and had access to standard diet and water ad libitum.

Before the mice were used in seizure experiments, they were adapted to their environment for at least 6 days. Seizures were induced between 2 and 5 p.m., and drugs were administered at the times indicated in the text and tables.

In all seizure models, groups of 10 mice were used for each treatment or dose.

EXAMPLE 1

A. Effect of treatment with (R,S)-vinyl GABA (GVG) and glycine on 3-mercaptopropionic acid induced seizures Mice received an i.p. injection of GVG. Four hours later glycine was injected s.c. (7.51 mg/0.1 ml, dist. water). One hour after administration of glycine, 3-mercaptopropionic acid (40 mg/kg) was injected i.p. in order to induce seizures. The number of myoclonic and myotonic seizures was recorded during the subsequent 30 minute period. The results are shown in Table 1:

TABLE 1

| Treatment (mg/kg) | | | | | | Percent of animals | |
| GVG | glycine | N1 | N2 | N3 | N4 | with seizures | |
| --- | --- | --- | --- | --- | --- | --- | --- |
| 0 | 0 | 10 | 3 | 23 | 2 | 100 | (a) |
| 50 | 0 | 10 | 4 | 23 | 2 | 100 | (b) |
| 100 | 0 | 8 | 2 | 11 | 0 | 80 | (c) |
| 125 | 0 | 6 | 4 | 13 | 3 | 60 | |
| 150 | 0 | 6 | 1 | 8 | 1 | 60 | |
| 200 | 0 | 4 | 1 | 6 | 1 | 40 | (c) |
| 250 | 0 | 4 | 1 | 5 | 0 | 40 | |
| 300 | 0 | 1 | 0 | 1 | 0 | 10 | |
| 0 | 750 | 8 | 2 | 10 | 0 | 80 | (b) |
| 0 | 2250 | 6 | 1 | 8 | 1 | 60 | |
| 25 | 1500 | 4 | 0 | 4 | 0 | 40 | |
| 25 | 2250 | 5 | 0 | 6 | 0 | 50 | |
| 50 | 750 | 5 | 0 | 5 | 0 | 50 | (c) |
| 50 | 1500 | 0 | 0 | 0 | 0 | 0 | |
| 50 | 2250 | 0 | 0 | 0 | 0 | 0 | |
| 100 | 750 | 1 | 0 | 1 | 0 | 10 | (b) |
| 200 | 750 | 0 | 0 | 0 | 0 | 0 | (b) |

N1 = Number of animals with clonic seizures
N2 = Number of animals with tonic hind limb extensions
N3 = Total number of seizure episodes
N4 = Dead animals at the end of the observation period of 30 min
(a) Mean values of four experiments
(b) Mean values of two experiments
(c) Mean values of three experiments B. The time-dependence of the antiseizure effect of exogenous glycine Mice received an i.p. injection of GVG. Four hours later solutions of glycine in tap water were administered by gavage. Seizures were induced at the appropriate time by i.p. injections of 3-mercaptopropionic acid (40 mg/kg, 0.40 mg/0.1 ml, physiol. saline). The number of myoclonic and myotonic seizures was recorded at the indicated time following injection of 3-mercaptopropionic acid. The results are shown in Table 1a:

TABLE 1a

| Treatment (mg/kg) | | Time after glycine admin. (min) | N1 | N2 | N3 | N4 | percent of animals with seizures |
| --- | --- | --- | --- | --- | --- | --- | --- |
| GVG | glycine | | | | | | |
| 0 | 0 | — | 10 | 1 | 16 | 0 | 100 |
| 50 | 0 | — | 9 | 1 | 11 | 1 | 90 |
| 50 | 750 | 30 | 7 | 1 | 7 | 1 | 70 |
| 50 | 750 | 60 | 6 | 0 | 6 | 0 | 60 |
| 50 | 750 | 120 | 8 | 1 | 9 | 1 | 80 |
| 50 | 750 | 240 | 10 | 2 | 13 | 1 | 100 |
| 50 | 1500 | 15 | 7 | 0 | 7 | 0 | 70 |
| 50 | 1500 | 30 | 4 | 1 | 4 | 0 | 40 |

N1 = Number of animals with clonic seizures
N2 = Number of animals with tonic hind limb extensions
N3 = Total number of seizure episodes
N4 = Dead animals at the end of the observation of 30 min.

EXAMPLE 2

Effect of treatment with (R,S)-vinyl GABA (GVG) and glycine ethyl ester, on 3-mercaptopropionic acid-induced seizures Mice received an i.p. injection of GVG. After 1, 2, 3, and 4 hours, the animals received an s.c. injection of glycine ethyl ester as the hydrochloride. Five hours after GVG treatment, seizures were induced by an i.p. injection of 3-mercaptopropionic acid (40 mg/kg; 0.4 mg/0.1 ml, physiol. saline). The number of myotonic and myoclonic seizures was recorded during the subsequent 30 minute period. The results are shown in Table 2:

TABLE 2

| Treatment (mg/kg) | | Time After glycine ethyl ester* adm. (hours) | N1 | N2 | N3 | N4 | Percent of animals with seizures |
|---|---|---|---|---|---|---|---|
| GVG | glycine* ethyl ester | | | | | | |
| 0 | 0 | — | 10 | 3 | 17 | 2 | 100 |
| 0 | 1030 | 1 | 7 | 3 | 14 | 2 | 70 |
| 100 | 0 | — | 8 | 2 | 11 | 0 | 80 |
| 100 | 1030 | 1 | 3 | 1 | 5 | 1 | 30 |
| 100 | 1030 | 2 | 3 | 0 | 3 | 0 | 30 |
| 100 | 1030 | 3 | 7 | 2 | 10 | 0 | 70 |
| 100 | 1030 | 4 | 8 | 0 | 10 | 0 | 80 |

N1 = Number of animals with clonic seizures
N2 = Number of animals with tonic seizures
N3 = Total number of animals with seizure episodes
N4 = Dead animals at the end of the observation of 30 min.
*Administered as the hydrochloride salt

EXAMPLE 3

Effect of treatment with (R,S)-vinyl GABA (GVG) and N,N-dimethylglycine (DMGly) or sarcosine on 3-mercaptopropionic acid-induced seizures One group of mice received an s.c. injection of DMGly or sarcosine, as the hydrochloride. One hour later, seizures were induced by an i.p. injection of 3-mercaptopropionic acid (40 mg/kg; 0.4 mg/0.1 ml, physiol. saline). Two groups of mice received an i.p. injection of GVG. Two, 3 or 4 h after GVG treatment the animals received an s.c. injection of DMGly or sarcosine, as the hydrochloride. Five hours after injection of GVG (1 h or 2 h after DMGly or sarcosine administration), seizures were induced as mentioned above. The number of myoclonic and myotonic seizures was recorded during the subsequent 30 minute period. The results with DMGly are shown in Table 3:

TABLE 3

| Treatment (mg/kg) | | Time after DMGly admin. (hours) | N1 | N2 | N3 | N4 | Percent of animals with seizures |
|---|---|---|---|---|---|---|---|
| GVG | DMGly* | | | | | | |
| 0 | 0 | 0 | 10 | 3 | 17 | 2 | 100 |
| 0 | 1030 | 1 | 8 | 3 | 17 | 0 | 80 |
| 100 | 1030 | 1 | 6 | 4 | 14 | 0 | 60 |
| 100 | 1030 | 2 | 8 | 5 | 26 | 2 | 80 |
| 100 | 0 | — | 8 | 2 | 11 | 0 | 80 |

N1 = Number of animals with clonic seizures
N2 = Number of animals with tonic seizures
N3 = Total number of seizure episodes
N4 = Dead animals at the end of the observation period of 30 min.
*Administered as the hydrochloride salt.

The results with sarcosine are shown in Table 3a.

TABLE 3a

| Treatment (mg/kg) | | Time after sarcosine admin. (hours) | N1 | N2 | N3 | N4 | Percent of animals with seizures |
|---|---|---|---|---|---|---|---|
| GVG | sarcosine* | | | | | | |
| 0 | 0 | — | 10 | 3 | 17 | 2 | 100 |
| 0 | 890 | 1 | 10 | 2 | 15 | 0 | 100 |
| 100 | 890 | 1 | 4 | 1 | 5 | 0 | 40 |
| 100 | 890 | 2 | 6 | 3 | 9 | 0 | 60 |
| 100 | 890 | 3 | 10 | 7 | 11 | 2 | 100 |

N1 = Number of animals with clonic seizures
N2 = Number of animals with tonic seizures
N3 = Total number of seizure episodes
N4 = Dead animals at the end of the observation period of 30 min.
*Administered as the hydrochloride salt

EXAMPLE 4

Effect of treatment with (R,S)-vinyl GABA (GVG) and glycine on bicuculline-induced seizures Mice were given an i.p. injection of GVG. Four hours later, glycine was injected i.p. One hour after administration of glycine seizures were induced by an s.c. injection of bicuculline (1.8 mg/kg; 0.018 mg/0.1 ml physiol. saline). The number of clonic and myotonic seizures were recorded during the subsequent 30 minute period. The results are shown in Table 4:

TABLE 4

| Treatment (mg/kg) | | N1 | N2 | N3 | N4 | Percent of animals with seizures |
|---|---|---|---|---|---|---|
| GVG | glycine | | | | | |
| 0 | 0 | 8 | 6 | 17 | 6 | 80 |
| 200 | 0 | 2 | 2 | 4 | 2 | 20 |
| 200 | 750 | 2 | 0 | 2 | 0 | 20 |

N1 = Number of animals with clonic seizures
N2 = Number of animals with tonic hind limb extensions
N3 = Total number of seizure episodes
N4 = Dead animals at the end of the observation period of 30 min.

EXAMPLE 5

Effect of treatment with (R,S)-vinyl GABA (GVG) and glycine on metrazol-induced seizures Mice received an i.p. injection of GVG. Four hours later glycine was injected s.c. One hour after administration of glycine, seizures were induced by i.p. injection of metrazol (75 mg/kg; 0.75 mg/0.1 ml, physiol. saline). The time between metrazol administration and the onset of clonic seizures was recorded. Those animals which had no seizures within 5 min were considered free of seizures. The results are shown in Table 5:

TABLE 5

| Treatment (mg/kg) | | Time between metrazol admin. and onset of clonic seizures (sec.)* | Percent of animals with seizures |
|---|---|---|---|
| GVG | glycine | | |
| 0 | 0 | 69 (47–115) | 100 |
| 0 | 750 | 57 (48–101) | 100 |
| 0 | 1500 | 88 (47–115) | 100 |
| 0 | 2250 | 125 (40–279) | 100 |
| 750 | 0 | 188 (110–738) | 100 |
| 750 | 750 | 184 (130–300) | 90 |
| 750 | 1500 | 162 (138–>300) | 80 |
| 750 | 2250 | 262 (128–>300) | 60 |

*Median; range in parentheses.

EXAMPLE 6

Effect of treatment with (R,S)-vinyl GABA (GVG) and glycine on picrotoxinine-induced seizures Mice received an i.p. injection of GVG. Four hours later glycine was injected i.p. One hour after administration of glycine seizures were induced by s.c. injection of picrotoxinine (5 mg/kg; 0.05 mg/0.1 ml, physiol. saline). The number of clonic and tonic seizure episodes was recorded during the subsequent 30 min period. The results are shown in Table 6:

TABLE 6

| Treatment (mg/kg) | | N1 | N2 | N3 | N4 | Percent of animals with seizures |
|---|---|---|---|---|---|---|
| GVG | glycine | | | | | |
| 0 | 0 | 10 | 10 | 31 | 10 | 10 |
| 200 | 0 | 10 | 10 | 45 | 10 | 10 |
| 200 | 750 | 10 | 10 | 45 | 10 | 10 |

TABLE 6-continued

| Treatment (mg/kg) | | | | | | Percent of animals with seizures |
| --- | --- | --- | --- | --- | --- | --- |
| GVG | glycine | N1 | N2 | N3 | N4 | |
| 750 | 0 | 10 | 10 | 47 | 10 | 10 |
| 750 | 750 | 10 | 8 | 37 | 8 | 10 |

N1 = Number of animals with clonic seizures
N2 = Number of animals with tonic hind limb extensions
N3 = Total number of seizure episodes
N4 = Dead animals at the end of the observation period of 30 min.

EXAMPLE 7

Effect of treatment with (R,S)-vinyl GABA and glycine on strychnine-induced convulsions Mice received an i.p. injection of GVG. Four hours later glycine was injected s.c. One hour after administration of glycine seizures were induced by i.p. injection of strychnine (base; 2 mg/kg; 0.02 mg/0.1 ml, physiol. saline). The time between strychnine administration and onset of tonic hind limb extensions was determined. The results are shown in Table 7:

TABLE 7

| Treatment (mg/kg) | | Time between strychnine admin. and onset of tonic seizures (sec.) | Percent of animals with seizures |
| --- | --- | --- | --- |
| GVG | glycine | | |
| 0 | 0 | 158 ± 23* | 100 |
| 0 | 750 | 178 ± 39* | 100 |
| 0 | 2250 | 224 ± 45* | 100 |
| 750 | 0 | 189 ± 15* | 100 |
| 750 | 2250 | 272 ± 61* | 100 |

*Mean values ± S.D. (N = 10).

We claim:

1. A method for controlling seizures in a patient in need thereof which comprises administering to said patient in combination:
    (a) from 0.2 to 2.0 grams per day of gamma-vinyl GABA, or a pharmaceutically acceptable salt thereof; and
    (b) from 2 to 12 grams per day of a $C_1$–$C_8$ alkyl ester of glycine, sarcosine, N,N-dimethylglycine or a pharmaceutically acceptable salt thereof.

2. A method as claimed in claim 1 wherein from 2 to 12 grams per day of a $C_1$–$C_8$ alkyl ester of glycine or a pharmaceutically acceptable salt thereof, is administered.

3. A method as claimed in claim 1 wherein from 2 to 12 grams per day of a $C_1$–$C_8$ alkyl ester of sarcosine or a pharmaceutically acceptable salt thereof, is administered.

4. A method as claimed in claim 1 wherein from 2 to 12 grams per day of a $C_1$–$C_8$ alkyl ester of N,N-dimethylglycine or a pharmaceutically acceptable salt thereof, is administered.

5. A method as defined in claim 1, wherein the gamma-vinyl GABA is in the form of the (S)-isomer substantially free of the (R)-isomer.

6. A pharmaceutical composition in dosage unit form for controlling seizures in a patient in need thereof which comprises:
    (a) from 50 to 100 mg of gamma-vinyl GABA, or a pharmaceutically acceptable salt thereof,
    (b) from 250 to 500 mg of a $C_1$–$C_8$ alkyl ester of glycine, sarcosine, N,N-dimethylglycine or a pharmaceutically acceptable salt thereof, and
    (c) a pharmaceutically acceptable carrier or diluent.

7. A composition as claimed in claim 6 wherein the composition contains a $C_1$–$C_8$ alkyl ester of glycine or a pharmaceutically acceptable salt thereof.

8. A composition as claimed in claim 6 wherein the composition contains a $C_1$–$C_8$ alkyl ester of sarcosine or a pharmaceutically acceptable salt thereof.

9. A composition as claimed in claim 6 wherein the composition contains a $C_1$–$C_8$ alkyl ester of N,N-dimethylglycine or a pharmaceutically acceptable salt thereof.

10. A composition as defined in claim 6 wherein the gamma-vinyl GABA is in the form of the (S)-isomer substantially free of the (R)-isomer.

* * * * *